US007241443B1

(12) United States Patent
Nash et al.

(10) Patent No.: US 7,241,443 B1
(45) Date of Patent: Jul. 10, 2007

(54) IMMUNOGEN ADHERENCE INHIBITOR AND METHOD OF MAKING AND USING SAME

(75) Inventors: Peter Nash, Eden Prairie, MN (US); John W. Rosevear, deceased, late of Edina, MN (US); by Donald L. Robinson, legal representative, Bloomington, MN (US)

(73) Assignee: Camas Incorporated, Lecenter, MN (US)

( * ) Notice: Subject to any disclaimer, the term of this patent is extended or adjusted under 35 U.S.C. 154(b) by 1080 days.

(21) Appl. No.: 09/616,843

(22) Filed: Jul. 14, 2000

Related U.S. Application Data

(60) Provisional application No. 60/201,268, filed on May 2, 2000.

(51) Int. Cl.
- A61K 39/395 (2006.01)
- C07K 16/12 (2006.01)
- A23J 1/08 (2006.01)

(52) U.S. Cl. .............................. 424/130.1; 530/387.1; 530/389.5; 530/413

(58) Field of Classification Search ............. 424/130.1, 424/164.1, 165.1, 167.1; 530/387.1, 389.5
See application file for complete search history.

(56) References Cited

U.S. PATENT DOCUMENTS

| | | | |
|---|---|---|---|
| 3,794,732 A | | 2/1974 | Raun |
| 3,917,818 A | | 11/1975 | Botes |
| 3,937,836 A | | 2/1976 | Raun |
| 4,166,867 A | * | 9/1979 | Betz et al. |
| 4,550,019 A | | 10/1985 | Polson |
| 4,748,018 A | | 5/1988 | Stolle et al. |
| 4,933,364 A | | 6/1990 | Ivy et al. |
| 5,080,895 A | | 1/1992 | Tokoro |
| 5,196,193 A | | 3/1993 | Carroll |
| 5,367,054 A | | 11/1994 | Lee |
| 5,443,976 A | | 8/1995 | Carroll |
| 5,585,098 A | | 12/1996 | Coleman |
| 5,725,873 A | | 3/1998 | Cook et al. |
| 5,741,489 A | * | 4/1998 | Pimentel |
| 5,753,228 A | | 5/1998 | Sterling et al. |
| 5,753,268 A | | 5/1998 | Stolle et al. |
| 5,919,451 A | | 7/1999 | Cook et al. |
| 5,965,128 A | | 10/1999 | Doyle et al. |
| 6,083,500 A | | 7/2000 | Wooley et al. |
| 6,086,878 A | * | 7/2000 | Adalsteinsson et al. |
| 6,217,865 B1 | | 4/2001 | Hunchar |
| 2002/0012666 A1 | | 1/2002 | Kuby et al. |

OTHER PUBLICATIONS

Drause et al, An rRNA Approach for assessing the role of olibgate amino acid-fermenting bacteria in ruminal amino acid deamination, Mar. 1996, Appl Environ Microbiol 62(3): 815-821.*

Kuby et al, Immunology, second edition, pp. 85-96, 1994.*

Abaza et al, J of Protein Chemistry 11(5): 433-444, 1992.*

Russell, J.B., Rumen bacteria rob cattle of nutrients, Agricultural Research, May 1993, p. A43-44.

Pate, F., Ionophores do not appear to work in molasses supplements, ONA Reports, The Florida cattlemen and Livestock Journal, Nov. 1996.

Lana, R.P., D.G. Fox, J.B. Russell, and T.C. Perry, Influence of monensin on Holstein steers fed high-concentrate soybean meal or urea, J. Anim. Sci. 75:2571-2579, 1997.

Herzberg et al, Degree of Immunity Induced by Killed Vaccines to Experimental Salmonellosis in Mice, Infection and Immunity, Jan. 1972, pp. 83-90.

Chen et al, More Monensin-Sensitive, Ammonia-Producing Bacteria from the Rumen, Applied and Environmental Microbiology, May 1989, pp. 1052-1057.

Russell, J.B., Rumen Bacteria Rob Cattle of Nutrients, Agricultural Research, May 1993, pp. A43-44.

Pate, F., Ionophores Do Not Appear to Work in Molasses Supplements, The Florida Cattleman and Livestock Journal, Nov. 1996.

Lana et al, Influence of Monensin on Holstein Steers Fed High-Concentrate Diets Containing Soybean Meal or Urea, Journal Anim. Sci. 1997, pp. 75:2571-2579.

Charley et al, Preserving Eggs by Freezing and Drying, Foods A Scientific Approach, 3rd Edition, 1998.

Gansheroff et al, *Escherichia coli* 0157:H7 in beef cattle presented for slaughter in U.S., Proc. Natl. Acad. Sci., Mar. 28, 2000, pp. 2959-2961.

Sugita-Konishi et al, Biosci Biotechnol Biochem 60(5): 886-8, May 1996.

Yokoyama et al, Vaccine 16(4): 388-93, Feb. 1998.

Stryer et al, in Biochemistry, 3rd ed., W H Freeman Co., pp. 31-33, 1998.

* cited by examiner

*Primary Examiner*—Christina Chan
*Assistant Examiner*—Phuong Huynh

(57) ABSTRACT

A microbial adherence inhibitor in the form of fowl egg antibodies is disclosed, along with the method of making it and methods of using it. The inhibitor functions by substantially preventing the attachment or adherence of colony-forming immunogens in the rumen and intestinal tract of host food animals. The inhibitor is made by inoculating female birds with the immunogen, harvesting the eggs which contain antibodies to the immunogen, drying the egg contents and adding to the feed or water for the host animals. Dependent upon the particular immunogen with which the female bird is inoculated, the egg antibody is used to promote the growth of food animals by improving feed conversion rates by decreasing the waste of dietary protein caused by the presence of certain colony-forming organisms in the animals, and to substantially reduce or eliminate the incidence of illnesses caused by the presence of certain illness-causing colony-forming immunogens, such as *E. coli* 0157:H7, in meat from food animals, and in other food stuffs.

15 Claims, No Drawings

IMMUNOGEN ADHERENCE INHIBITOR AND METHOD OF MAKING AND USING SAME

This application claims priority under 35 U.S.C. 119(e) of Provisional Application No. 60/201,268 filed May 2, 2000.

FIELD OF THE INVENTION

This invention is directed to microbial adherence inhibitor, in the form of fowl egg antibodies, for substantially preventing the attachment or adherence of colony-forming immunogens or haptens in the rumen and intestinal tract of host food animals, to the method of producing such adherence inhibitors, and to the methods of using such inhibitors to: (1) promote the growth of food animals by improving feed conversion rates by decreasing the waste of dietary protein caused by the presence of certain colony-forming protein-wasting organisms in food animals, and (2) to substantially reduce or eliminate the incidence of illnesses caused by the presence of certain illness-causing colony-forming immunogens or haptens in meat from food animals, which are not themselves subjected to the targeted illness, and in other food stuffs.

BACKGROUND OF THE INVENTION

Common bacterial immunogens which cause dramatic decreases in an animal's ability to utilize dietary protein include but are not limited to *Peptostreptococcus anaerobius, Clostridium aminophilum*, and *Clostridium sticklandii*. According to Russell (USDA-ARS, May 1993) these organisms, and others disclosed therein, have been collectively responsible for wasting up to 25 percent of the protein in cattle diets. This is a loss of as much as $25 billion annually to cattle producers and is especially apparent in "grazing animals which are often deficient in protein, even though their protein intake appears to be adequate". As the host consumes protein in the diet, these deleterious organisms wastefully degrade the protein to ammonia which is converted to urea by the liver and kidneys and thus lost to the host when excreted as urine. These deleterious organisms also compete with beneficial organisms which the host needs for the efficient utilization of ammonia. In addition, they need other beneficial organisms in the rumen the greater the ammonia utilization.

The principal objective of the present invention is to substantially prevent the colonization of deleterious organisms such as *P. anaerobius, C. sticklandii* and *C. aminophilum* as well as the growth of such organisms in the rumen and the intestinal tracts of food animals resulting in their substantial elimination from the animal by the administration of the fowl egg antibody to the specific organisms.

Common bacterial immunogens which cause food borne illness in humans include *E. coli, Listeria, Salmonella* and *Campylobacter*, all of which produce flu-like symptoms such as nausea, vomiting, diarrhea and/or fever, and in some cases kidney damage or death. In recent years foodstuffs contaminated with these bacteria have caused gastro-intestinal distress in tens or hundreds of thousands of people and the recall and destruction of millions of pounds of food. The resulting economic loss has been staggering. Especially daunting as a public health threat has been *E. coli* 0157:H7, a pathogenic strain of the common gut bacterium, first identified in 1982. The bacteria are carried in the intestinal tracts of food animals and expelled in their feces. From there, the bacteria enter the food supply, not only in the meat of those animals, but foods such as milk, fruit juices, lettuce, alfalfa sprouts, radishes, and others.

Haptens are partial or incomplete immunogens such as certain toxins, which cannot by themselves cause antibody formation but are capable of combining with specific antibodies. Such haptens may include bacterial toxin, yeast mold toxin, viruses, parasite toxins, algae toxins, etc.

Other colony-forming organisms include Actinomycetes, *Streptococcus*, Bacteriodes such as *B. ruminicola*, Crytococcus and yeasts and mold.

Another principal object of the present invention is to substantially prevent the adherence of immunogens, such as *E. coli* 0157:H7, or haptens, and the colonization and growth of such immunogens or haptens in the rumen or intestinal tracts of food animals, and substantial elimination of the immunogen or hapten from the feces of the animals, by the administration to the animals of fowl egg antibody to the specific immunogen or hapten.

THE PRIOR ART

The production of avian egg antibody for the diagnosis or treatment of specific conditions has been known. The production of avian egg antibody for the inhibition of organisms, specifically the colonization of non-illness-causing protein-wasting organisms, and the adherence and colonization of illness-causing immunogens is not suggested.

Representative prior art patents include the following:
Polson, U.S. Pat. No. 4,550,019
Stolle, et al U.S. Pat. No. 4,748,018
Tokoro, U.S. Pat. No. 5,080,895
Carroll, U.S. Pat. No. 5,196,193
Lee, U.S. Pat. No. 5,367,054
Coleman, U.S. Pat. No. 5,585,098
Stolle, et al U.S. Pat. No. 5,753,268

Raun, U.S. Pat. No. 3,794,732, discusses the uses of polyester antibiotics in ruminant rations to improve the utilization of feed in ruminant animals. This specifically addresses the use of antibiotics in ruminant animals as growth promotants.

Raun, U.S. Pat. No. 3,937,836, discusses the use of specific antibiotic compounds for ruminant feed utilization improvement when given orally to the animal. Specifically, the animal develops rumen function where more propionates in relation to acetates are produced thus improving feed utilization.

Ivy et al, U.S. Pat. No. 4,933,364, discusses an alternative process for promoting growth and feed efficiency of food producing mammals. They propose the use of zinc antibiotic that can be added in insoluble form to create a zinc antibiotic complex which enhances feed efficiency of food producing mammals. They reference two U.S. Pat. Nos. 3,501,568 and 3,794,732, that cover monensin in great detail.

Other references on the use of additives such as monensin have mentioned the need for wise application of these materials because they can be toxic to some animals such as horses. These antibiotics, which are not approved for use in dairy cows, must be administered carefully. In addition, feed intake is initially reduced as monensin can not be added to molasses based supplements which are classic additives to cattle fees. (Pate, F., "Ionophores Do Not Appear To Work In Molasses Supplements", ONA Reports, November, 1966, 2 pages, Florida Cattleman and Livestock Journal. Lona, R. P. et al, J. Anim. Sci. 75(1)): 2571-2579, 1979.)

Polson, U.S. Pat. No. 4,550,019, is directed to the manufacture and use of fowl egg yolk antibodies for making immunological preparations for the passive immunization of animals, including humans, as immuno reagents for immunosorbitive processes and in particular for quantitative analytical tests, especially micro assays for diagnostic, pathological, forensic and pharmacokinectic investigations.

Stolle et al, U.S. Pat. No. 4,748,018 is directed to a method of passive immunization of mammals using avian egg yolk antibody against any of a variety of antigens using various methods of administration under various conditions and using various compositions incorporating the antibody, after first developing in the mammal a tolerance for the antibody.

Tokoro, U.S. Pat. No. 5,080,895 is directed to a specific antibody containing substance from eggs and method of production and use thereof for the treatment of infectious or other diseases, and as additives in food for livestock and poultry, cosmetics, and medicines, and in the field of serodiagnosis. Although not explicitly stated, it is apparent that the use of the egg antibody in feeds is to provide an easy means of oral administration of the antibody for the treatment of intestinal infections in livestock or poultry.

Carroll, U.S. Pat. No. 5,196,193 and divisional U.S. Pat. No. 5,443,976 are directed to anti-venom compositions containing horse antibody or avian egg yolk antibody for neutralizing snake, spider, scorpion or jelly fish venom.

Lee, U.S. Pat. No. 5,367,054 is directed to methods for large scale purification of egg immunoglobulin for the treatment of infections.

Coleman, U.S. Pat. No. 5,585,098 is directed to a method of oral administration of chicken yolk immunoglobulins to lower somatic cell count in the milk of lactating ruminants.

Stolle et al, U.S. Pat. No. 5,753,268 is directed to an anti-cholesterolemic egg vaccine and method for production and use as a dietary supplement for the treatment of vascular disorders in humans and other animals.

SUMMARY OF THE INVENTION

Broadly stated this invention is directed to a method for the production of a microbial adherence inhibitor for administration to host food animals to substantially prevent the adherence of colony-forming immunogens or haptens in the rumen and/or intestinal tracts of the food animals by first inoculating female birds, in or about to reach their egg laying age, with the particular target immunogen. Then, after a period of time sufficient to permit the production in the bird of antibody to the targeted immunogen, the eggs laid by the birds are harvested. The total antibody-containing contents of the eggs are separated from the shells and dried. The egg contents may be dried on a feed extender or carrier material. The dried separated egg antibody adherence inhibiting material may be stored or shipped for use when needed.

The target immunogen with which the bird is inoculated depends upon the anticipated use of the inhibitor, a non-disease-causing protein-wasting organism where boosting of feed efficiency is the objective, and a targeted disease-causing organism where the objective is the substantial reduction or elimination of illnesses.

The dried egg contents incorporating the antibody specific to the targeted immunogen is administered to the food animals by distributing the antibody material substantially uniformly throughout an animal feed and then supplying the resulting antibody-containing animal feed to the food animals. When improved feed utilization is the objective, the antibody-containing animal feed is supplied to food animals during the normal finishing schedule prior to slaughter. The substantial prevention of colonization of the targeted organism in the rumen or intestinal tract of the animal will ultimately permit elimination of the organism from the animal. This repression of colonization and elimination of the subject organisms will permit a significant decrease in the wasteful degradation of the dietary protein fed to food production animals. In addition, the resulting decrease in competition to the non-ammonia producing organisms will further enhance the most efficient utilization of feed by the host. (Russell, USDA-ARS, May 1993). When the objective is the elimination of disease-causing organisms from the meat of food animals, the antibody-containing feed is supplied sufficiently before slaughter to substantially prevent adherence of the target immunogen or hapten in the intestinal tract of the animal, and permit elimination of the immunogen or hapten from the animal.

The invention is directed particularly to the production of an adherence inhibitor specific to *E. coli* 0157:H7 and to the substantial reduction or elimination of gastric illnesses caused by this bacterium. The invention is described with particular reference to elimination of illnesses caused by *E. coli* 0157:H7, but it is understood that the invention is not so limited, but is equally applicable to elimination of illnesses caused by the other colony-forming immunogens and haptens.

DESCRIPTION OF THE PREFERRED EMBODIMENTS

The present invention is based on the concept of specifically inhibiting the ability of colony-forming protein-wasting organisms, such as *P. anaerobius, C. sticklandii* and *C. aminophilum*, and colony forming disease-causing organisms, such as *E. coli* 0157:H7, *Listeria, Salmonella* and *Campylobacter*, to adhere in the rumen or intestinal tracts of food animals and thus reduce their ability to multiply, grow and colonize. Dietary modifications may be designed to make the rumen and intestinal tract less receptive to the organisms over the lifetime of the animal. While the microbial inhibitor of the present invention may be administered at will by the producer, it is preferred for efficient animal feed utilization that a carefully determined and managed course of administration during the finishing period at the feedlot level be scheduled and followed. Such a predetermined period which takes advantage of the low dose, longer cumulative effect of the inhibitor and which is also easily integrated into current production practices will provide the most economically attractive rate of return through improved animal performance.

For the elimination of disease-causing organisms the inhibitor may be administered either immediately pre-slaughter or over some substantial period of the lifetime of the animal. It is preferred that a carefully determined and managed mid-term period course of administration at the feedlot level be followed. As described, a set pre-slaughter period takes advantage of the low dose, longer cumulative effect, is easily integratable into current production practices and is the most economical. It also allows the microorganism to naturally disappear from the mud and manure on the outside of the animal, a significant source of potential contamination at slaughter. Under the current feeding system, food animal feed efficiency is enhanced through the use of ionophores such as monesin, a feed additive marketed under the trade name Rumensin. These are a class of polyester antibiotics approved for feed given to beef cattle and dairy heifers but not approved for use with lactating diary cows. Most gram-positive organisms are non-specifically vulnerable to the ionophores, antibiotics which can also be quite toxic to the host animal if used improperly. As these antibiotics are not specific, many of the ruminal organisms required to digest the cellulose of ingested plant material may also be affected. The problem with carry over and the development of drug resistant strains of organisms are also major concern to the industry. The use of broad spectrum antibiotics has further drawbacks including vulnerability to human error, additional cost, consumer resistance and the like. In addition, the monensin type additive can not be administered with commonly used molasses based supplements.

Any organism that colonizes in the rumen or alimentary tract of its host must possess the capability of sticking or adhering to that surface in order to multiply and grow. The specific organisms addressed by this invention are no exception to the rule. As other factors such as the need of beneficial organisms for specific enzymes must also be considered, specific reagents are required to reduce the number of targeted organisms in the rumen or intestinal tract while not interfering with other normal flora. The organism inhibitor of this invention strongly interferes with adherence in a highly specific manner and, on a cumulative basis, thereby prevents the targeted organisms from multiplying, growing and colonizing. Through the vehicle of a simple daily feed supplement, the product essentially supplies the host with an antibody preparation designed not to cure any disease in the animal but to specifically dislodge any resident bacteria in the rumen or alimentary tract and to prevent attachment of any newly introduced numbers of that same bacteria. The microbial inhibitor has no direct effect whatsoever on the ultimate food products and leaves absolutely no undesirable residue in the animal or in the ultimate food products. In addition, since the deleterious organisms are prevented from multiplying; they will over time, for example the 120-day finishing period in the feedlot, disappear through natural degradation from the feedlot environment helping to eliminate that significant potential source of recontamination. The inhibitor product itself can be classified as a natural material of animal origin and as such can be used in almost any kind of feeding program. As the active ingredients are completely natural, they will work well with most feeds and feed additives including molasses based supplements.

All mammals and birds provide similar types of protection which allow for an immediate immune response in their very young offspring until they too acquire the ability to make the antibodies for themselves. More specifically called passive antibody protection, this defense mechanism is passed to the young of mammals through the placenta, the mother's milk or through both. The young of birds, however, receive their passive antibody protection through the store of antibodies placed in the eggs in which they develop from the embryonic stage. Birds, in particular, have the ability to "load up" their eggs as they are formed, with a very large supply of antibodies concentrated many fold over that which is present in the serum of the mother. In addition, avian antibodies are much more stable and resistant to inactivation through digestion than mammalian antibodies, especially under adverse conditions. Once immunized the hen layers the unique IgY types immunoglobulins in the yolk while depositing the common chicken IgM and IgA immunoglobulins in the albumin. The albumin helps resistance to the whole egg preparations and helps protect the avian antibodies. Furthermore, the large quantities of antibodies which are placed in eggs are much more exclusively those specific for the antigens to which the mother has most recently been exposed to and challenged by. This all results in the eggs of birds being a most ideal source for large quantities of economically produced, highly specific and stable antibodies. While the invention is illustrated by the use of chickens to produce avian antibody, other fowl including turkeys, ducks, geese, etc. may be used.

Specifically, groups are obtained of young hen chickens typically Rhode Island Reds, white leghorns, sex-linked hybrid crosses or other breeds suited to large egg size, high volume egg production and ease of handling which are about to reach laying age, about 19 weeks for chickens, on a schedule predetermined by the amount and timing of final product desired resulting in a steady continuous production stream. After a suitable period of isolation and acclimatization of about 2 to 4 weeks, each group will enter into an inoculation program using rehydrated proprietary preparations of specific antigens to which an antibody is desired. The antigens may be obtained from commercial sources such as the American Type Culture Collection (ATCC). The antigen may be injected intramuscularly, but preferably injected sub-cutaneously. In approximately four to five weeks, the average egg collected will contain copious amounts of the desired specific antibody in a readily usable and stable form. The chickens may be reinoculated with the targeted antigen throughout the egg laying period to maintain the high antibody level.

Batches of eggs from predetermined groups of chickens are cracked, the contents are separated from the shells and mixed and preferably pasteurized (to eliminate potential pathogenic microorganism from the chicken and thus reduce potential contamination of feed). The total egg content is dried using standard commercial methods, such as spray drying using ambient or hot air up to 50° C. and tested to determine overall titer or antibody level. The egg contents may be dried alone or on innocuous feed extenders such as dry soy or rice husks or the like. Standard test procedures are used, such as ELISA, or agglutination, or the like. The typical batch is then blended with batches from groups of chickens at other average production levels resulting in a lot of standardized active ingredient. The dried egg antibody microbial inhibitor material may be stored and shipped on carrier materials such as soy bean hulls, boluses and/or tablets. Dependent on the needs and specifications of the feed formulator and the final customer, the final antibody product may include some type of innocuous additive, such as dried whey or dried soy protein powder, dried soy or rice husks or the like for formulation with feed ration. One egg produced and processed by the above procedures will yield a product sufficiently active and stable to provide at least as many as 350 to 700 daily doses of managed protection against specific microbial colonization. This method provides for the first time, an economical, safe and effective means for controlling feed efficiency organisms in beef cattle and dairy herds, and an economical, safe and effective means for controlling *E. coli* 0157:H7 and other illness-causing organisms in cattle herds.

The present invention specifically addresses feed efficiency as it relates to beef cattle, and by extension dairy cattle and dairy herds, and to the problem of eliminating illness-causing organisms from cattle. However, the concept of preventing microbial adherence has great economic potential for a number of diverse food safety and production applications. One such field of application is in feed and water targeting specific undesirable microorganisms. An example of this application would include products to actively inhibit pathogenic or even spoilage microorganisms in animal feed formulated for chickens and other poultry.

Another such field of application is as rinse aid ingredients targeted to specific undesirable microorganisms. Examples of this application include products to actively dislodge pathogenic or even spoilage microorganisms for use in solutions for spot cleaning and rinsing beef carcasses or for chilling poultry after they have been dressed.

The most successful colonizing microorganisms, bacteria, viruses and parasite, etc., have evolved a number of different types of molecules, referred to as "adherins," on their surfaces which can very tightly stick to one or more types of specific molecules that are part of the host's various surfaces. The adhesion inhibitor is an avian antibody of extraordinarily high specific activity which can very tightly bind to, coat, cover and obliterate these adherins which attach themselves to their hosts with a lock and key type of fit to very unique chemical structures. In addition to this direct attack, components of the complement system included in most biological fluids, such as blood, lymph, saliva, tears and to some extent intestinal secretions, recognize an antibody attachment as triggers for their many types of defensive activities. Specific antibody attachment and coating combined with the very likely mobilization of many other cellular defense systems, therefore, quickly culminates in the chemical inactivation and ultimately the destruction of the targeted microorganism.

The invention is further illustrated by the following examples:

EXAMPLE 1

Selection of Egg Laying Avian Hens

The strain of egg laying hen may vary with needs and uses. Any egg laying fowl hens may be immunized including chickens, turkeys, ducks, emus or any other fowl. The common strains of egg laying chickens are the preferred and are usually selected for the number of eggs laid per year, size of egg and ease of housing. Rhode Island Red, White Leghorn and Red Sex Linked hybrids are the animals of choice based on egg size (large to ex-large, 50-65 gm) and were used for the immunization schedules. The ease of handling the animals and the size and uniformity of the eggs along with the number of eggs laid per hen per year were observed. Although any avian egg laying hen could be used, for cost and ease of use these chickens proved to work the best. The Red Sex-linked hybrids gave the most uniformity and greater number of eggs per animal. These animals produce a large to extra-large grade of egg (50-65 gm) and up to 300 eggs a year per hen.

EXAMPLE 2

Preparation of Stock Culture

The American Type Culture Collection *E. coli* 0157:H7 Stock #43895 was used as the model bacterium. The organism was isolated from raw hamburger and colonizes in cattle. The ATCC Method for rehydration of the stock was followed. The bacterium is rehydrated in 1.0 ml of TSB Broth (Tryptase Soy Broth, Becton Dickinson), transferred to 5 ml of TSB sterile broth and incubated overnight (approx. 18 hrs) at 37° C. Nice turbid growth was observed. This is used as stock as needed. It was streaked on Sorbitol-MacConkey Agar (Difco) for verification of colony production.

EXAMPLE 3

Preparation of H Antigens for Immunogens

The H antigens were selected for development into an immunogen for immunizing the egg laying hens. Certain conditions are used to maintain the optimum growth of the H antigen during culturing to give added concentrations for the prep. Veal Infusion Agar (VIS) and Veal Infusion Broth (VIB, Becton Dickinson) is preferred for H antigen production. Stock TSB inoculated with VIB is incubated at 22°-24° C. or room temperature for 18 hours. This stimulates flagella development on the bacteria. Flasks layered with VIA are inoculated with VIB culture. Good growth was seen after 22 hours. The product was harvested after 4 days. Flasks are combined by washing off the agar surface with Dulbecco's PSB solution (pH 7.3-7.4). The product is collected in tubes. Density is checked using spectrophotometer enumeration and McFarland nephelometer standards. Approximately $3 \times 10/12$/ml in Stock. Motility is checked with motility agar slant (Northeast Laboratory Services). Stock is diluted to concentration of approximately $1 \times 10^9$ per ml in PBS and stirred for 1 hr at room temperature. The flagella is removed from the outside of the bacteria. Supernatant is collected using centrifugation. Pellet of whole bacteria is separated from the supernatant. Dry weight approx. 14.7 mg/ml is determined and the material is used as stock immunogen for H antigen. It is diluted to 1 mg/ml in PBS and heated for 30 minutes at 60°-70° C. This helps keep contamination down to a minimum. Thiogylcollate broth is inoculated to check for growth and animals are inoculated with immunogen.

EXAMPLE 4

Preparation of O Antigen for Immunogens

Brain Heart Infusion (BFI, acumedia) is used to stimulate the O antigens on the bacterium. Stock TSB innoculate BHI Broth is formed and incubated at 37° C. for 18 hrs. This stimulates somatic antigen development on the bacteria. Flasks containing BHI Broth are inoculated with BHI Broth culture. While stirring slowly, flasks are incubated at 37° C. Good growth is seen after 22 hours. Flasks are combined and the material is harvested using centrifugation and sterile saline (0.9%) at approx. 300 rpm for 30 minutes. The harvest is collected in tubes. Density is checked using spectrophotometer enumeration and McFarland nephelometer standards. The material is diluted to approximately $1 \times 10^9$ per ml. 4% percent sodium deoxycholate (Difco) solution is added as a 1:1 ratio with culture in 0.9% sterile saline (Herzberg, 1972) and stirred for approx. 18 hrs at room temperature (22° to 24° C.). The material is centrifuged to remove whole cells. Supernatant is used as stock for O antigen. Dry weight is determined at approximately 14.9 mg/ml. The product is diluted in sterile PBS, pH 7.4 to 1 mg/ml for O Immunogen.

EXAMPLE 5

Preparation of WC Antigen for Immunogens

Tryptic Soy Broth (TSB, Northeast Laboratory Services) plus Yeast Extract (BBL) is used for Whole Cell (WC) antigen production. TSB plus Yeast Extract 0.6% Broth is inoculated with TSB Stock and incubated at 37° C. for 18 hrs. This stimulates somatic and other surface antigens to development on the bacteria. Flasks are inoculated with TSB with Yeast Extract Broth. While stirring slowly, it is incubated at 37° C. Good growth is seen after 22 hours. The flasks are combined and the product is harvested using centrifugation at approx. 3000 rpm for 30 minutes and collected in tubes. The product is resuspended in sterile PBS, pH 7.4. Density is checked using spectrophotometer enumeration and McFarland nephelometer standards. Dry weight is approximately 19.7 mg/ml. The product is diluted to approximately $2 \times 10^9$ per ml or 2 mg/ml dry weight, and 0.6% formaldehyde solution in PBS is added as a 1:1 ratio with culture and stirred for approx. 18 hrs at RT (22°-24° C.) to fix cells. Thiogylcollate broth is inoculated to check for growth and pH of preparation (pH 7-7.4) is checked. The supernatant is used as stock for WC antigen. The stock is diluted in PHS, pH 7.4 to 1 mg/ml for WC immunogen.

EXAMPLE 6

Preparation of A Antigen for Immunogen

The Minca Medium is used for A antigen production. It is a standard medium for stimulating the pilii and related adherin antigens. Stock TSB Minca Medium Broth (Inf. Immun., February 1977, 676-678) is inoculated and incubated at 37° C. for 18 hrs. This stimulated adhesion antigen development on the bacteria. Flasks are inoculated with Minca Medium Broth and while stirring slowing is incubated at 37° C. Good growth is seen after 18 hours. The flasks are combined and the product is harvested using centrifugation at approx. 2500 rpm for 30 minutes and collected in tubes. The pellet is resuspended in PBS and stirred with a stir bar for 1 hour at 22°-24° C. (RT). This removes the flagella. The product is collected in tubes and the pellet is resuspended in PBS and 0.01% Tween 20™, transferred to Waring Blender in cold (4° C.) at low speed for 30 minutes. Density is checked using spectrophotometer enumeration and McFarland nephelometer standards. The product is centrifuged to remove whole cells. The supernatant is used as stock for A antigen. It may be heated at 60° C. for 40 minutes to inactivate if needed. Gentamycin is added at 50 µ/ml as preservative. Thiogylcollate broth is inoculated to check for growth. Dry weight is determined at approximately 10.6 mg/ml. The product is diluted with PBS, pH 7.4 to 1 mg/ml for A immunogen.

EXAMPLE 7

Preparation of P Antigen for Immunogen

The Reinforced Clostridial Medium is used for P antigen production. It is a standard medium for stimulating adherence antigens for *Peptostreptococcus anaerobius*. These cultures must be grown under strict anaerobic conditions. The stock culture is grown according to ATCC for #49031. As with other organisms, subcultures are grown in small amounts. Thioglycollate Media (Difco) is inoculated with the stock and incubated for 48 hrs. Flasks are inoculated with Reinforced Clostridial Medium Broth. The medium is covered with a mixture of anaerobic gas. Flasks are combined and the product is harvested using centrifugation at approximately 2500 rpm for 30 minutes, collected in tubes and run at low speed for 30 minutes. Density is checked. The product is centrifuged to remove whole cells. The supernatant is used as stock for P antigen. It is heated at 60° C. for 40 minutes to inactivate if needed. Dry weight is determined. Approximately 20.5 mg/ml. The product is diluted with PBS, pH 7.4 to 1 mg/ml for P immunogen.

EXAMPLE 8

Preparation of CS Antigen for Immunogen

The Reinforced Clostridial Medium is used for CS antigen production. It is a standard medium for stimulating adherence antigens for *Clostridium sticklandii*. These cultures must be grown under strict anaerobic conditions. The stock culture is grown according to ATCC for #12662. As with other organisms, subcultures are grown in small amounts. Thioglycollate Media (Difco) is inoculated with the stock and incubated for 48 hrs. Flasks are inoculated with Reinforced Clostridial Medium Broth. The medium is covered with a mixture of anaerobic gas. Flasks are combined and the product is harvested using centrifugation at approximately 2500 rpm for 30 minutes. The product is collected in tubes and spun at low speed for 30 minutes. Density is checked using spectrophotometer enumeration and McFarland nephelometer standards. The product is centrifuged to remove whole cells. The supernatant is used as stock for CS antigen. It is heated at 60° C. for 40 minutes to inactivate if needed. Dry weight is determined at approximately 22 mg/ml. The product is diluted with PBS, pH 7.4 to 1 mg/ml for CS immunogen.

EXAMPLE 9

Preparation for CA Antigen for Immunogen

The Reinforced Clostridial Medium is used for CA antigen production. It is a standard medium for stimulating adherence antigens for *Clostridium aminophilius*. These cultures must be grown under strict anaerobic conditions. The stock culture is grown according to ATCC for #49906. As with other organisms, subcultures are grown in small amounts. Thioglycollate Media (Difco) is inoculated with the stock and incubated for 48 hrs. Flasks are inoculated with Reinforced Clostridial Medium Broth. The medium is covered with a mixture of anaerobic gas. Flasks are combined and the product is harvested using centrifugation at approximately 2500 rpm for 30 minutes. The product is collected in tubes and spun at low speed for 30 minutes. Density is checked using spectrophotometer enumeration and McFarland nephelometer standards. The product is centrifuged to remove whole cells. The supernatant is used as stock for CA antigen. It is heated at 60° C. for 40 minutes to inactivate if needed. Dry weight is determined at approximately 20.5 mg/ml. The product is diluted with PBS, pH 7.4 to 1 mg/ml for CA immunogen.

EXAMPLE 10

Preparation of ELISA Plates Using H, O, WC and A Antigens for Monitoring Antibodies in Eggs, Chickens and Feed H, O, WC and A ELISA: Ninety six well assay plate (flat bottom Costar®) were coated using 100 µ/ml with various concentration of antigens (H, A, O, or WC or combination: 10 µg-200 µg/ml) in carbonate buffer, ph 9.6. Plates were incubated between 22°-37° C. for up to 18 hrs. The wells were aspirated to prevent cross-contamination. The plates were blocked with 390 µl/well of 0.5% BSA and incubated at 37° C. for 1 hr. Plates were coated using alternative rows of positive or negative for controls. Plates were rinsed 1× with wash buffer containing Tween™ 20. One hundred microliters per well of diluted sample are added to wells in duplicate wells, and incubated at 37° C. for one hour. Goat anti-Chicken IgG conjugate with Horseradish peroxidase (Kirkegard and Perry Laboratories; 1:1000 to 1:3000) was added. After 1 hr incubation, the substrate (TMB, KPL) was added according to manufacturer's instructions and the reaction is stopped after 10 minutes with 0.1M phosphoric acid. Optical densities of the wells were determined in Dynatech ELISA Reader at 450 nm and the information was recorded for further data analysis.

EXAMPLE 11

Analysis of Individual Eggs and Serum Over Time

Eggs were selected at various periods in the immunization period for monitoring antibody responses to the specific antigens. Selected chickens were monitored at day 0 and continued on a monthly basis after the $4^{th}$ month. The whole egg was collected from the shell and then a 1 ml sample was taken. This sample was then extracted with buffer to analyze the antibody content. The standard ELISAs for the H, O, WC and A immunogens were used for analysis. The negative readings were subtracted form the OD readings. Serum samples were collected from each animal two weeks after the fourth immunogen injection.

The data given in the table below are examples of the results obtained over the first four months.

| Egg Sample Date | H Chicken | O Chicken | WC Chicken | A Chicken |
|---|---|---|---|---|
| 1 day: After first injection | 0.03 OD | Neg | 0.05 OD | Neg |
| 1 month | 0.60 OD | Neg | 0.05 OD | Neg |
| 5 weeks | 0.74 | ND | ND | ND |
| 2 months | 1.22 OD | 1.11 OD | 0.88 OD | 0.79 OD |
| 3 months | 1.00 OD | 1.4 OD | 0.99 OD | 1.4 OD |
| 4 months | 1.16 OD | 1.4 OD | 0.94 OD | 1.22 OD |
| Serum: 1 month | 1.4 OD | 0.91 OD | 1.17 OD | 0.97 |

EXAMPLE 12

Preparation of ELISA Plates Using P, CS and CA Antigens for Monitoring Antibodies in Eggs, Chickens and Feed P, CS and CA ELISA: Ninety six well assay plate (flat bottom Costar®) were coated using 100 μl/ml with various concentrations of antigens (P, CS, CA or combination: 10 μg-200 μg/ml) in carbonate buffer, pH 9.6. Plates were incubated between 22-37° C. for up to 18 hrs. The wells were aspirated to prevent cross-contamination. The plates were blocked with 390 μl/well of 0.5% BSA and incubated at 37° C. for 1 hr. Plates were coated using alternative rows of positive or negative for controls. Plates are rinsed 1× with wash buffer containing Tween™ 20. One hundred microliters per well of diluted sample are added to wells in duplicate wells, and incubated at 37° C. for one hour. Goat anti-Chicken IgG conjugate with Horseradish peroxidase (Kirkegard and Perry laboratories; 1:1000-1:3000) was added. After 1 hr incubation, the substrate (TMB, KPL) was added according to manufacturer's instructions and the reaction is stopped after 10 minutes with 0.1M phosphoric acid. Optical densities of the wells were determined in Dynatech ELISA Reader at 450 nm and the information was recorded for further data analysis.

EXAMPLE 13

Immunization of Chicken with H Immunogen

Six selected egg laying hens, 3 White Leghorns and 3 Rhode Island Reds approximately 19 weeks old were injected with the stock H immunogen. Four injections (500 μg, 100 μg, 200 μg and 250 μg) were given 1 week apart. A serum sample was collected two weeks after the last initial injection. If boosters were needed, 100 μg was given in each booster (every 6 months). Within four weeks, 4 out of 6 hens produced excellent antibodies in the eggs. ELISA H readings averaged 1.00 OD for 1:10,000 dilution and 0.265 OD for 1:50,000. Leghorn hens did not do as well but all 3 Rhode Island Reds did well. After six weeks the average ELISA H reading was 1.40 OD for 1:20,000 dilution with all chickens responding.

EXAMPLE 14

Immunization of Chicken with O Immunogen

Six selected egg laying hens, 6 White Leghorns, approximately 19 weeks old were injected with the stock O immunogen. Four injections (500 μg, 100 μg, 200 μg and 250 μg) were given 1 week apart. A serum sample was collected two weeks after the last initial injection. If boosters were needed, 100 μg was given in each booster (every 6 months). Within four weeks, 5 out of the 6 hens produced excellent antibodies in the eggs. ELISA O readings averaged 1.42 OD for 1:10,000 dilution and 0.680 OD for 1:50,000. After six weeks the average ELISA O reading was 1.15 OD for 1:20,000 dilution with still 5 chickens responding.

EXAMPLE 15

Immunization of Chicken with WC Immunogen

Six selected egg laying hens, 6 Rhode Island Reds, approximately 19 weeks old were injected with the stock WC immunogen. Four injections (500 μg, 100 μg, 200 μg and 250 μg) were given 1 week apart. A serum sample was collected two weeks after the last initial injection. If boosters were needed, 100 μg was given in each booster (every 6 months). Within four weeks, 4 out of the 6 hens produced excellent antibodies in the eggs. ELISA WC readings averaged 0.95 OD for 1:10,000 dilution and 0.250 OD for 1:50,000. After six weeks the average ELISA WC reading was 0.95 OD for 1:20,000 dilution with still 5 chickens responding.

EXAMPLE 16

Immunization of Chicken with A Immunogen

Six selected egg laying hens, 6 White Leghorns, approximately 19 weeks old were injected with the stock A immunogen. Four injections (500 μg, 100 μg, 200 μg and 250 μg) were given 1 week apart. A serum sample was collected two weeks after the last initial injection. If boosters were needed, 100 μg were given in each booster (every 6 months). Within four weeks, 5 out of the 6 hens produced excellent antibodies in the eggs. ELISA A readings averaged 1.40 OD for 1:10,000 dilution and 0.576 OD for 1:50,000. After six weeks the average ELISA A reading was 1.15 OD for 1:20,000 dilution with still all chickens responding.

EXAMPLE 17

Immunization of Chicken with P Immunogen

Six selected egg laying hens, White Leghorns, approximately 19 weeks old were injected with the stock P immunogen. Four injections (500 µg, 100 µg, 200 µg and 250 µg) were given 1 week apart. A serum sample was collected two weeks after the last initial injection. If boosters were needed, 100 µg were given in each booster (every 6 months). Within four weeks, 5 out of the 6 hens produced excellent antibodies in the eggs.

EXAMPLE 18

Immunization of Chicken with CS Immunogen

Six selected egg laying hens, White Leghorns, approximately 19 weeks old were injected with the stock CS immunogen. Four injections (500 µg, 100 µg, 200 µg and 250 µg) were given 1 week apart. A serum sample was collected two weeks after the last initial injection. If boosters were needed, 100 µg was given in each booster (every 6 months). Within four weeks, all 5 out of 6 hens produced excellent antibodies in the eggs.

EXAMPLE 19

Immunization of Chicken with CA Immunogen

Six selected egg lay hens, Red Sex-Linked Hybrids, approximately 19 weeks old were injected with the stock CA immunogen. Four injections (500 µg, 100 µg, 200 µg and 250 µg) were given 1 week apart. A serum sample was collected two weeks after the last initial injection. If boosters were needed, 100 µg was given in each booster (every 6 months). Within four weeks, all 6 hens produced excellent antibodies in the eggs.

EXAMPLE 20

Preparation of Stock Production Whole Egg Reagents

Selected hens were combined from all four immunogen groups for *E. coli* 0157:H7 or three immunogen groups for anaerobes, to be used to produce production batches of whole egg reagents. Sterling U.S. Pat. No. 5,753,228 presents an excellent review of uses for the selection of eggs and storage of the same. The eggs were randomized and shell removed. The whole egg is mixed well and pasteurized using standard conditions (60° C. (140° F.) for 3.5 minutes) Charley, H. and C. Weaver, 3$^{rd}$ Edition, Foods: a scientific approach, Merrill-Prentice Hall, p 350, 1998). Once pasteurized, samples were tested for activity and store at 4° C. until dried or sprayed onto carriers. Samples of 250 µl were analyzed.

Examples of results for ELISAs are given:

| Pasteurized Whole Egg: *E. coli* 0157:H7 | | |
|---|---|---|
| Immunogen | Dilution | O.D. |
| WC | 500 | 0.532 |
| WC | 2500 | 0.113 |

| Pasteurized Whole Egg: *E. coli* 0157:H7 -continued | | |
|---|---|---|
| Immunogen | Dilution | O.D. |
| H | 500 | 0.466 |
| H | 2500 | 0.115 |
| O | 500 | 0.338 |
| O | 2500 | 0.128 |
| A | 500 | 0.588 |
| A | 2500 | 0.155 |

| Pasteurized Whole Egg: Anaerobes | | | | |
|---|---|---|---|---|
| Immunogen | Dilution | Batch #1 | Batch #2 | Batch #3 |
| CA | 100 | 0.339 | 0.275 | 0.627 |
| CA | 500 | 0.104 | 0.296 | 0.201 |
| P | 100 | 0.724 | 0.882 | 0.576 |
| P | 500 | 0.248 | 0.594 | 0.651 |
| CS | 100 | 0.457 | 0.268 | 0.650 |
| CS | 500 | 0.304 | 0.143 | 0.476 |

EXAMPLE 21

Coating of Feed Additive Carriers

Although whole egg can be dispensed in water supplies, or in a dried format as whole powdered egg, use of a carrier helps distribute the material in a uniform method. This makes it easier for mixing with standards feeds. A number of carriers can be used to provide a vehicle as a feed additive as needed. Soy hulls in crude, refined and pelted format, rice hulls, corn, cottonseed hulls, distilled dried grains, beet pulp or any other. The production pasteurized whole egg prep is coated on to the carrier and either fed directly to the animals or dried to 10-15% moisture. Approximately 1000 ml of whole, pasteurized egg is sprayed on 50 lbs of pelleted soybean hulls. The preferred carrier for cattle is pelleted soybean hulls while for young swine the fines from pelleted soybean hulls. The feed additive is mixed with the standard animal feed. The preferred level is 10-15 lbs of feed additive to 2000 lbs of animal feed.

EXAMPLE 22

Analysis of Feed Additive Samples after Coating with Reagents

Samples were collected from batches of feed additive after they were coated on to the carriers. The samples were analyzed and the results are as follows:

| Product Name | Moisture % | Protein % | Fat % | Fiber, crude % |
|---|---|---|---|---|
| Crude Soybean Hulls, uncoated | 11.59 | 26.76 | 9.10 | 18.63 |
| CAMAS EYE 0157 Crude soybean Hulls | 12.35 | 25.67 | 8.26 | 19.46 |
| CAMAS EYE * Control Crude Soybean hulls | 12.06 | 24.89 | 9.92 | 20.38 |
| Soybean Pellets uncoated | 11.65 | 9.89 | 2.43 | 33.47 |

-continued

| Product Name | Moisture % | Protein % | Fat % | Fiber, crude % |
|---|---|---|---|---|
| CAMAS EYE Efficiency Pellets | 12.37 | 10.19 | 2.57 | 33.12 |

* CAMAS EYE identifies inhibitors produced according to the present invention

EXAMPLE 23

Analysis of Production Eggs Over Time: *E. coli* 0157:H7

Samples of the whole egg preparations were analyzed using the ELISA systems for H, O, WC and A immunogens to monitor activity over time after the initial immunization schedule was completed. Selected animals from each group were placed into the production group. The average ELISA OD readings (negative subtracted) for the fourth through the sixth months are given in the table below. The eggs were sampled using 250 μl of the whole eggs and diluted 1:500 and 1:2500 in PBS buffer and then run in the appropriate ELISA to determine the average OD reading at each dilution. The negative control readings are subtracted from each reading. The immunogens showed different responses in animals along with good specificity. The A immunogen gave the best responses in these tests. Data for these immunogens over time is given below:

| Immuogen | | Fourth Month | Fifth Month | Six Month |
|---|---|---|---|---|
| H: | 1:500 | 0.388 | 0.848 | 0.718 |
| | 1:2500 | 0.085 | 0.237 | 0.195 |
| O: | 1:500 | 0.593 | 0.792 | 0.704 |
| | 1:2500 | 0.147 | 0.294 | 0.184 |
| WC: | 1:500 | 0.398 | 0.730 | 0.578 |
| | 1:2500 | 0.062 | 0.273 | 0.130 |
| A: | 1:500 | 0.700 | 1.014 | 0.909 |
| | 1:2500 | 0.102 | 0.305 | 0.224 |

EXAMPLE 24

Analysis of Production Eggs Over Time: Feed Efficiency

Samples of whole egg preparations were analyzed using the ELISA systems for P, CS and CA immunogens to monitor activity over time after the initial immunization-schedule was completed. Selected animals from each group were placed into the production group. The average ELISA OD readings for the fourth through the sixth months are given in the table below. The eggs were sampled using 250 μl of the whole eggs and diluted 1:500 and 1:2500 in PBS buffer and then run in appropriate ELISA to determine the average OD reading at each dilution. The negative control readings are subtracted from each reading. The immunogens showed different responses in the animals along with good specificity.

| Immuogen | | Fourth Month | Fifth Month | Six Month |
|---|---|---|---|---|
| P: | 1:500 | 1.182 OD | 1.128 OD | 0.942 OD |
| | 1:2500 | 0.785 OD | 0.489 OD | 0.343 OD |
| CS: | 1:500 | 0.843 OD | 0.989 OD | 0.582 OD |
| | 1:2500 | 0.318 OD | 0.356 OD | 0.187 OD |
| CA: | 1:500 | 1.156 OD | 1.087 OD | 0.998 OD |
| | 1:2500 | 0409 OD | 0.282 OD | 0.507 OD |

EXAMPLE 25

Analysis of Feed Additives for Antibody Activity: *E. coli* 0157:H7

Samples of the coated hulls were analyzed using the ELISA systems for H, O, WC and A immunogens to monitor activity after pasteurizing, spraying, drying and storage. Good antibody response was recorded after the processing of the production whole egg batches and drying on crude soybean hulls. Data for two batches is given below:

| Batch: Coated Hulls | | WC Immuno-gen | H Immuo-gen | O Immuno-gen | A immuno-gen |
|---|---|---|---|---|---|
| Batch #1 | 1:10 | 0.673 OD | 1.103 OD | 1.105 OD | 1.299 OD |
| | 1:100 | 0.106 OD | 0.236 OD | 0.229 OD | 0.302 OD |
| Batch #2 | 1:10 | 1.174 OD | 1.291 OD | 1.180 OD | 1.224 OD |
| | 1:100 | 0.177 OD | 0.396 OD | 0.327 OD | 0.458 OD |

EXAMPLE 26

Analysis of Feed Additives for Antibody Activity: Feed Efficiency

Samples of the coated hulls were analyzed using the ELISA systems for P, CS and CA immunogens to monitor activity after pasteurizing, spraying, drying and storage. Good antibody response was recorded after the processing of the production whole egg batches and drying on crude soybean hulls. One gram samples of the 15 lbs of coated hulls were extracted and analyzed. Data for three batches is given in the table below:

| Batch: Coated Hulls | | P Immunogen | CS Immunogen | CA Immunogen |
|---|---|---|---|---|
| Batch #1 | 1:100 | 0.067 OD | 0.289 OD | 0.051 OD |
| | 1:500 | 0.057 OD | 0.131 OD | 0.037 OD |
| Batch #2 | 1:100 | 0.028 OD | 0.039 OD | 0.095 OD |
| | 1:500 | 0.049 OD | 0.015 OD | 0.021 OD |
| Batch #3 | 1:100 | 0.046 OD | 0.115 OD | 0.136 OD |
| | 1:500 | 0.012 OD | 0.055 OD | 0.012 OD |

EXAMPLE 27

Recovery of Active Antibody and Egg Protein After Feed Mix

Bags of coated soybean refined hulls were coated with the production whole egg reagent containing anti-*E. coli* 0157:

H7 adherence inhibitors. One bag of feed additive (15 lbs) was added to 2000 lbs of standard cattle feed. Control feed additive was produced with whole eggs from free ranging chickens. Soybean hulls were coated with this preparation and mixed as the test feed additive containing the specific antibodies. Samples of the mixed feed were collected and analyzed for active antibody to the ELISA WC immunogen as well as commercial ELISA for detecting egg protein in food (Vertatox® Quantitative Egg Allergen Test, Neogen). The data is given in the chart below for two batches of feed ration.

| Mixed Feed | First Batch | Second Batch |
|---|---|---|
| Test Feed-Additive: | | |
| 1:6000 | 0.172 OD | 0.112 OD |
| 1:12000 | 0.009 OD | 0.036 |
| Control Feed-No Additive | | |
| 1:6000 | 0.049 | Neg. |
| 1:12000 | 0.005 | Neg. |
| Test Feed-Additive: Egg Protein | 0.958 OD 17 ppm | 1.268 OD >20 ppm |
| Control Feed-No Additive: Egg Protein | 0.800 OD 15 ppm | 1.050 OD 20 ppm |

EXAMPLE 28

Feeding of Cattle

Two groups of cattle were fed either the 0157:H7 feed additive (coated onto refined soybean hulls) or control feed additive (coated with control eggs and no specific adherence inhibitors). The animals were fed at a rate of 15 lbs of feed additive per 2000 lbs of feed. They averaged 10 lbs per animal per day. Animals weighed approximately 1000 lbs when they started and over 1400 lbs when sent to market. All animals looked very healthy with the test animals eating more feed during the 87 days. Five of the test animals were positive during the start of the experiment for *E. coli* 0157:H7 and only one of the control animals. Within 30 days on feed additive all test animals were negative for *E. coli* 0157:H7 and stayed negative for three consecutive samples over a 30-day period. Standard protocols were followed for sampling. All animals were ear-tagged and placed in separate pens. Animals were sampled on a weekly basis for the first month and then bi-weekly after that until shipped to market. Grab samples were taken from the rectum and placed into sterile labeled bags. All samples were held on ice until processed in the lab. All samples were processed within 4 hours of collection each day. The fecal samples were diluted with TSB with 0.6% yeast extract. Dilutions of the mixture were streaked into Sorbitol-MacConkey's agar with or without cefixime-tellurite supplement (Dynal®). Colorless colonies are picked for further testing. A latex agglutination test was used to identify *E. coli* serogroup 0157 (Oxoid dry Spot™ *E. coli* 0157). If positive, then individual colonies were selected for further isolation on SMC agar streak plates. Isolated colonies were run on the commercial EIA for EH *E. coli* 0157 (Binax, NOW® EH *E. coli* 0157). Biochemical confirmation can be done with API-20E (Analytab Products). (Appl. Environ. Microbiol., 62(7) 2567-2570, 1966; J. Clin. Micro. 36(10): 3112, 1998).

One of the most startling and distressing characteristics of *E. coli* 0157:H7 is the small number of microorganisms necessary to produce cases of human illness. By way of example, at least 10,000 of the more virulent *Salmonella* serotypes but as few as ten *E. coli* 0157:H7 are required to cause a person to become symptomatic. Therefore, one animal hosting or externally contaminated with the microorganism can, when slaughtered, affect as much as 16 tons of ground beef to the extent that a single helping of the product could result in illness if improperly prepared. Although the probability of any one animal hosting the microorganism at any one time is low, the probability of its presence in any one particular feedlot is high.

There are presently three different methods for protecting the consumer from the *E. coli* 0157:H7 threat which have been officially recognized. The three methods are (1) thorough cooking, (2) steam pasteurization and (3) irradiation, all of which have specific drawbacks, including human and mechanical error, cost, consumer resistance, and the like.

Any microorganism which colonizes the alimentary tract of its host must possess the capability of sticking or adhering to that surface in order to multiply. *E coli* 0157:H7 is no exception to this rule. The adherence inhibitor of this invention strongly interferes with adherence and, on a cumulative basis, thereby prevents the specific targeted microorganism from colonizing and multiplying. Through the vehicle of a simple daily feed additive, the product essentially supplies the host with a specific antibody preparation designed not to cure any disease in the animal (cattle are essentially unaffected by *E. coli* 0157:H7 being only transitory hosts) but merely to dislodge any resident bacteria and to prevent the attachment of any newly introduced bacteria in the alimentary tract. The adherence inhibitor has no direct effect on the host itself, leaves absolutely no undesirable residue in the animals and thus has no effect whatsoever on the ultimate food products. In addition, since the microorganism is prevented from multiplying, it will over time (for example the 120 day finishing period in the feedlot) disappear through natural degradation from the mud and manure coating the animal, eliminating this significant potential source of contamination at slaughter. Properly managed, the risk of cross contaminating other food sources through feedlot runoff or by the application of manure as fertilizer is also essentially eliminated.

It is apparent that many modifications and variations of this invention as herein before set forth may be made without departing from the spirit and scope thereof. The specific embodiments described are given by way of example only and the invention is limited only by the terms of the appended claims.

The invention claimed is:

1. A method of promoting the growth of food animals by decreasing the waste of dietary protein caused by the presence of a protein-wasting immunogen in the rumen or intestinal tracts of food animals by inhibiting the ability of the immunogen to adhere to the rumen or intestinal tracts of food animals to reduce the ability of the immunogen to multiply, said protein-wasting immunogen is P antigen from *P. anaerobius*, said method comprising:

A. Inoculating female birds, in or about to reach their egg laying age, with P antigen from *P. anaerobius;*

B. Allowing a period of time sufficient to permit the production in the birds and eggs laid by the birds of antibody in the eggs to P antigen from *P. anaerobius*, said antibody in the eggs including IgY immunoglobulins in the yolks of the eggs and IgM and IgA immunoglobulins in the albumin of the eggs;
C. Harvesting the eggs laid by the birds;
D. Separating the entire contents of said harvested eggs from the egg shells;
E. Drying said separated entire contents of said harvested eggs;
F. Distributing said dried entire contents of said harvested eggs substantially uniformly in animal feed or water to provide antibody-containing animal feed or water; and
G. Supplying the resulting dried entire contents of said harvested eggs and animal feed or water to food animals whereby the IgY immunoglobulins bind to the protein-wasting immunogens to inhibit adherence of the protein-wasting immunogen in the intestinal tracts of the animals thereby promoting the growth of the animals.

2. A method of promoting the growth of food animals by decreasing the waste of dietary protein caused by the presence of a protein-wasting immunogen in the rumen or intestinal tracts of food animals by inhibiting the ability of the immunogen to adhere to the rumen or intestinal tracts of food animals to reduce the ability of the immunogen to multiply, said protein-wasting immunogen is CS antigen from *C. sticklandii*, said method comprising:
A. Inoculating female birds, in or about to reach their egg laying age, with CS antigen from *C. sticklandii;*
B. Allowing a period of time sufficient to permit the production in the birds and eggs laid by the birds of antibody in the eggs to CS antigen from *C. sticklandii*, said antibody in the eggs including IgY immunoglobulins in the yolks of the eggs and IgM and IgA immunoglobulins in the albumin of the eggs;
C. Harvesting the eggs laid by the birds;
D. Separating the entire contents of said harvested eggs from the egg shells;
E. Drying said separated entire contents of said harvested eggs;
F. Distributing said dried entire contents of said harvested eggs substantially uniformly in animal feed or water; and
G. Supplying the resulting dried entire contents of said harvested eggs and animal feed or water to food animals whereby the IgY immunoglobulins bind to the protein-wasting immunogens to inhibit adherence of the protein-wasting immunogen in the intestinal tracts of the animals thereby promoting the growth of the animals.

3. A method of promoting the growth of food animals by decreasing the waste of dietary protein caused by the presence of a protein-wasting immunogen in the rumen or intestinal tracts of food animals by inhibiting the ability of the immunogen to adhere to the rumen or intestinal tracts of food animals to reduce the ability of the immunogen to multiply, said protein-wasting immunogen is CA antigen from *C. aminophilium*, said method comprising:
A. Inoculating female birds, in or about to reach their egg laying age, with CA antigen from *C. aminophilium;*
B. Allowing a period of time sufficient to permit the production in the birds and eggs laid by the birds of antibody in the eggs to CA antigen from *C. aminophilium*, said antibody in the eggs including IgY immunoglobulins in the yolks of the eggs and IgM and IgA immunoglobulins in the albumin of the eggs;
C. Harvesting the eggs laid by the birds;
D. Separating the entire contents of said harvested eggs from the egg shells;
E. Drying said separated entire contents of said harvested eggs;
F. Distributing said dried entire contents of said harvested eggs substantially uniformly in animal feed or water; and
G. Supplying the resulting dried entire contents of said harvested eggs and animal feed or water to food animals whereby the IgY immunoglobulins bind to the protein-wasting immunogens to inhibit adherence of the protein-wasting immunogen in the intestinal tracts of the animals thereby promoting the growth of the animals.

4. The method of claim 1 including: providing a dry feed carrier material, drying said entire contents of said harvested eggs by coating the carrier material with said entire contents of said harvested eggs, distributing said carrier material coated with said entire contents of said harvested eggs in animal feed or water, and supplying the carrier material coated with said entire contents of said harvested eggs and animal feed or water to inhibit adherence of the immunogen in the intestinal tracts of the animals thereby promoting the growth of the animals.

5. The method of claim 4 wherein: providing a dry feed carrier material from a group of materials including soybean hulls, rice hulls, corn, cottonseed hulls, distilled dried grains and beet pulp.

6. The method of claim 2 including: providing a dry feed carrier material, drying said entire contents of said harvested eggs by coating the carrier material with said entire contents of said harvested eggs, distributing said carrier material coated with said entire contents of said harvested eggs in animal feed or water, and supplying the carrier material coated with said entire contents of said harvested eggs and animal feed or water to inhibit adherence of the immunogen in the intestinal tracts of the animals thereby promoting the growth of the animals.

7. The method of claim 6 wherein: providing a dry feed carrier material from a group of materials including soybean hulls, rice hulls, corn, cottonseed hulls, distilled dried grains and beet pulp.

8. The method of claim 3 including: providing a dry feed carrier material, drying said entire contents of said harvested eggs by coating the carrier material with said entire contents of said harvested eggs, distributing said carrier material coated with said entire contents of said harvested eggs in animal feed or water, and supplying the carrier material coated with said entire contents of said harvested eggs and animal feed or water to inhibit adherence of the immunogen in the intestinal tracts of the animals thereby promoting the growth of the animals.

9. The method of claim 8 wherein: providing a dry feed carrier material from a group of materials including soybean hulls, rice hulls, corn, cottonseed hulls, distilled dried grains and beet pulp.

10. A method of promoting the growth of food animals by decreasing the waste of dietary protein caused by the presence of a protein-wasting immunogen in the rumen or intestinal tracts of food animals to reduce the ability of the immunogen to multiply, said protein-wasting immunogen is P antigen from *P. anaerobius*, said method comprising:
A. Inoculating female birds, in or about to reach their egg laying age, with P antigen from *P. anaerobius;*
B. Allowing a period of time sufficient to permit the production in the birds and eggs laid by the birds of antibody in the eggs to P antigen from *P. anaerobius*, said antibody in the eggs including IgY immunoglobulins in the yolks of the eggs and IgM and IgA immunoglobulins in the albumin of the eggs;

C. Harvesting the eggs laid by the birds;

D. Separating the entire contents of said harvested eggs from the shells;

E. Providing a dry feed carrier material;

F. Coating said dry feed carrier material with the separated entire contents of said harvested eggs;

G. Distributing said carrier material coated with the entire contents of said harvested eggs substantially uniformly in animal feed; and H. Supplying the resulting dry feed carrier material coated with the entire contents of said harvested eggs and animal feed to food animals whereby the IgY immunoglobulins bind to the protein-wasting immunogens to inhibit adherence of the immunogen in the intestinal tracts of the animals thereby promoting the growth of the animals.

11. The method of claim 10 wherein: providing a dry feed carrier material from a group of materials including soybean hulls, rice hulls, corn, cottonseed hulls, distilled dried grains and beet pulp.

12. A method of promoting the growth of food animals by decreasing the waste of dietary protein caused by the presence of a protein-wasting immunogen in the rumen or intestinal tracts of food animals by inhibiting the ability of the immunogen to adhere to the rumen or intestinal tracts of food animals to reduce the ability of the immunogen to multiply, said protein-wasting immunogen is CS antigen from *C. sticklandii*, said method comprising:

A. Inoculating female birds, in or about to reach their egg laying age, with CS antigen from *C. sticklandii*;

B. Allowing a period of time sufficient to permit the production in the birds and eggs laid by the birds of antibody in the eggs to CS antigen from *C. sticklandii*, said antibody in the eggs including IgY immunoglobulins in the yolks of the eggs and IgM and IgA immunoglobulins in the albumin of the eggs;

C. Harvesting the eggs laid by the birds;

D. Separating the entire contents of said harvested eggs from the egg shells;

E. Providing a dry feed carrier material;

F. Coating said dry feed carrier material with the separated entire contents of the harvested eggs;

G. Distributing said carrier material coated with the entire contents of the eggs substantially uniformly in animal feed; and H. Supplying the resulting dry feed carrier material coated with the entire contents of the eggs and animal feed to food animals whereby the IgY immunoglobulins bind to the protein-wasting immunogens to inhibit adherence of the immunogen in the intestinal tracts of the animals thereby promoting the growth of the animals.

13. The method of claim 12 wherein: providing a dry feed carrier material from a group of materials including soybean hulls, rice hulls, corn, cottonseed hulls, distilled dried grains and beet pulp.

14. A method of promoting the growth of food animals by decreasing the waste of dietary protein caused by the presence of a protein-wasting immunogen in the rumen or intestinal tracts of food animals by inhibiting the ability of the immunogen to adhere to the rumen or intestinal tracts of food animals to reduce the ability of the immunogen to multiply, said protein-wasting immunogen is CA antigen from *C. aminophilium*, said method comprising:

A. Inoculating female birds, in or about to reach their egg laying age, with CA antigen from *C. aminophilium*;

B. Allowing a period of time sufficient to permit the production in the birds and eggs laid by the birds of antibody in the eggs to CA antigen from *C. aminophilium*, said antibody in the eggs including IgY immunoglobulins in the yolks of the eggs and IgM and IgA immunoglobulins in the albumin of the eggs;

C. Harvesting the eggs laid by the birds;

D. Separating the entire contents of said harvested eggs from the egg shells;

E. Providing a dry feed carrier material;

F. Coating said dry feed carrier material with the separated entire contents of the harvested eggs;

G. Distributing said carrier material coated with the entire contents of the eggs substantially uniformly in animal feed; and H. Supplying the resulting dry feed carrier material coated with the entire contents of said harvested eggs and animal feed to food animals whereby the IgY immunoglobulins bind to the protein-wasting immunogens to inhibit adherence of the immunogen in the intestinal tracts of the animals thereby promoting the growth of the animals.

15. The method of claim 14 wherein: providing a dry carrier from a group of materials including soybean hulls, rice hulls, corn, cottonseed hulls, distilled grains and beet pulp.

* * * * *